(12) United States Patent
Gescheit et al.

(10) Patent No.: US 10,080,840 B2
(45) Date of Patent: Sep. 25, 2018

(54) CONTROL UNIT FOR INFUSION PUMP UNITS, INCLUDING A CONTROLLED INTERVENTION UNIT

(71) Applicant: Roche Diabetes Care, Inc., Indianapolis, IN (US)

(72) Inventors: Iddo Gescheit, Tel Aviv (IL); Hans-Juergen Kuhr, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 111 days.

(21) Appl. No.: 15/133,485

(22) Filed: Apr. 20, 2016

(65) Prior Publication Data

US 2016/0228641 A1    Aug. 11, 2016

Related U.S. Application Data

(63) Continuation of application No. PCT/EP2014/071861, filed on Oct. 13, 2014.

(30) Foreign Application Priority Data

Oct. 21, 2013  (EP) .................................. 13189458

(51) Int. Cl.
  *A61M 5/172*    (2006.01)
  *A61M 5/142*    (2006.01)
(52) U.S. Cl.
  CPC ...... *A61M 5/1723* (2013.01); *A61M 5/14244* (2013.01); *A61M 5/14248* (2013.01);
  (Continued)

(58) Field of Classification Search
  CPC ........... A61M 2005/14208; A61M 2005/1726; A61M 2202/0007; A61M 2205/3303;
  (Continued)

(56) References Cited

U.S. PATENT DOCUMENTS

2003/0060767 A1    3/2003  Peter et al.
2003/0125612 A1*   7/2003  Fox .................... A61B 5/14532
                                                    600/347
(Continued)

FOREIGN PATENT DOCUMENTS

EP        1 762 259 A1    3/2007
WO    WO 00/25844 A1      5/2000
(Continued)

*Primary Examiner* — Quynh-Nhu H Vu
(74) *Attorney, Agent, or Firm* — Bose McKinney & Evans LLP

(57) ABSTRACT

A control unit for an electronically controlled pump unit controls the pump unit to infuse insulin into a diabetic's body in a substantially continuous way according to a preset infusion schedule as a function of time. The control unit includes an intervention unit that continuously evaluates a blood-glucose indicative input for detecting an actual or expected hypoglycaemia and executes, in response to an actual or expected hypoglycaemia, a temporary hypoglycaemia intervention. The intervention includes, for an intervention time interval, overriding the preset infusion schedule by temporarily suspending insulin infusion or temporarily reducing insulin infusion below the preset infusion schedule. The intervention unit adapts its way of operation with respect to executing the hypoglycaemia intervention in accordance with a control signal that is separate from the blood-glucose indicative input. The control unit automatically generates the control signal as a function of time and/or based on sensor input.

14 Claims, 3 Drawing Sheets

(52) U.S. Cl.
CPC ............. *A61M 2005/14208* (2013.01); *A61M 2005/1726* (2013.01); *A61M 2202/0007* (2013.01); *A61M 2205/3303* (2013.01); *A61M 2230/005* (2013.01); *A61M 2230/201* (2013.01); *A61M 2230/205* (2013.01); *A61M 2230/42* (2013.01); *A61M 2230/50* (2013.01); *A61M 2230/63* (2013.01)

(58) Field of Classification Search
CPC ...... A61M 2230/005; A61M 2230/201; A61M 2230/205; A61M 2230/42; A61M 2230/50; A61M 2230/63; A61M 5/14244; A61M 5/14248; A61M 5/17

See application file for complete search history.

(56) References Cited

U.S. PATENT DOCUMENTS

| | | |
|---|---|---|
| 2004/0220517 A1 | 11/2004 | Starkweather et al. |
| 2010/0049127 A1 | 2/2010 | Haueter et al. |
| 2010/0331657 A1* | 12/2010 | Mensinger ........... A61B 5/7445 600/365 |
| 2012/0059353 A1* | 3/2012 | Kovatchev .......... G06F 19/3437 604/504 |
| 2013/0041343 A1 | 2/2013 | Toumazou et al. |

FOREIGN PATENT DOCUMENTS

| | | |
|---|---|---|
| WO | WO 01/70307 A1 | 9/2001 |
| WO | WO 01/72358 A1 | 10/2001 |
| WO | WO 2006/083831 A1 | 8/2006 |
| WO | WO 2008/110263 A1 | 9/2008 |
| WO | WO 2009/077143 A1 | 6/2009 |
| WO | WO 2010/028719 A1 | 3/2010 |
| WO | WO 2010/055504 A1 | 5/2010 |

* cited by examiner

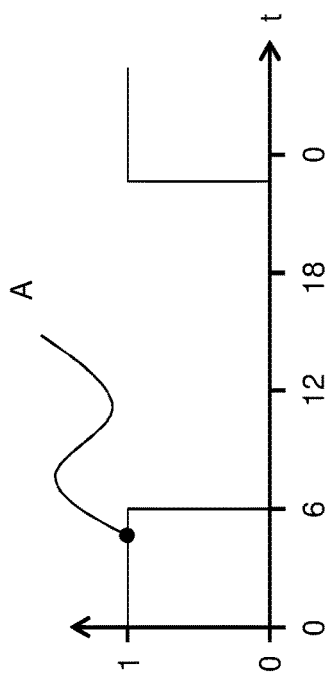
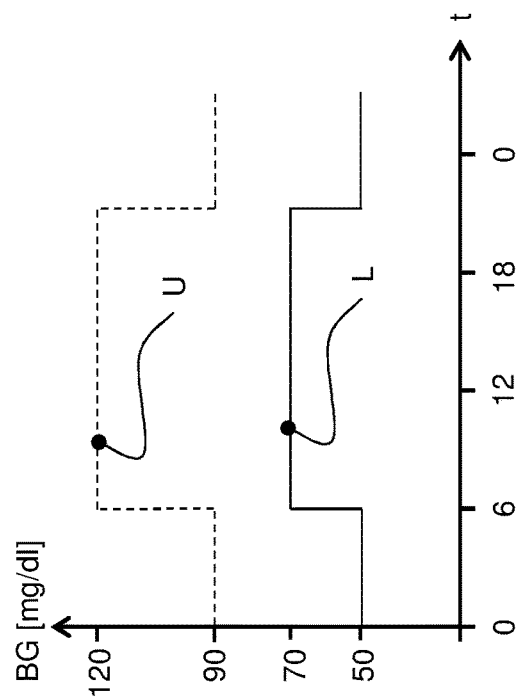
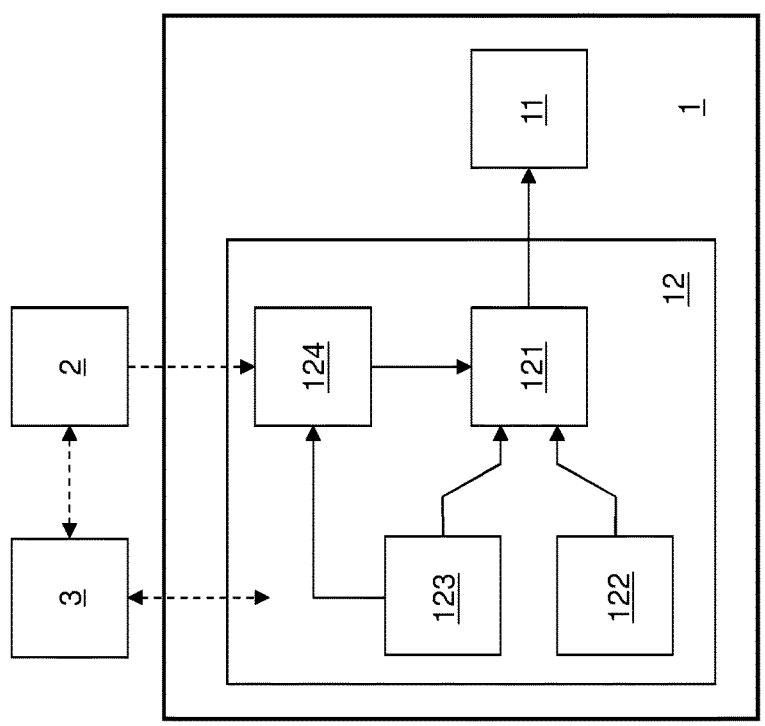
Fig. 1

CONTROL UNIT FOR INFUSION PUMP UNITS, INCLUDING A CONTROLLED INTERVENTION UNIT

RELATED APPLICATIONS

This application is a continuation of PCT/EP2014/071861, filed Oct. 13, 2014, which claims priority to EP 13189458.6, filed Oct. 21, 2013, both of which are hereby incorporated herein by reference in their entireties.

BACKGROUND

The present disclosure is directed towards diabetes therapy systems as used in the therapy of diabetes mellitus by Continuous Subcutaneous Insulin Infusion (CSII) and control units for a pump unit of such systems.

The present disclosure is further directed towards methods for controlling operation of an pump unit in such a system.

Continuous Subcutaneous Insulin Infusion (CSII) is an advanced and therapeutically advantageous way of treating diabetes mellitus. Under CSII, a diabetic carries a miniaturized infusion pump substantially continuously, night and day. The infusion pump infuses minimal quantities of insulin in a substantially continuous way according to a person-specific, generally time-variable infusion schedule, thus providing a so-called basal amount of insulin that is required by the diabetic's body for maintaining a normal or close-to-normal metabolism and in particular glucose concentration. For typical state-of-the-art systems, the basal administration schedule follows a generally circadian cycle and is preset by a healthcare professional. In addition, insulin pumps are designed to administer larger insulin quantities, so called boli, within a short period of time on demand, in order to cover diabetic's food intake, and under exceptional circumstances, such as illness or in case of a hyperglycaemia (also referred to as hyperglycaemic excursion or hyperglycaemic episode), which is a situation of increased glucose concentration, resulting from a relative lack of insulin within the diabetic's body.

Here and following in the present disclosure, "glucose" and phrases like "glucose value" or "glucose concentration" refer to glucose measured in a diabetic's blood, i.e., glucose, or glucose that is correlated with the glucose, in particular glucose in the subcutaneous tissue or interstitial fluid.

The opposite to a situation of hyperglycaemia is a hypoglycaemia (also referred to as hypoglycaemic excursion or hypoglycaemic episode), where the glucose level is too low, i.e., below a generally desired level, resulting from a relative excess of insulin within the diabetic's body. Both hyperglycaemia and hypoglycaemia may, when not appropriately dealt with, result in severe and potentially fatal complications. Untreated hypoglycaemia may in particular lead, within minutes to few hours, to symptoms and behaviour generally known for and associated with drunkenness or drug consumption, followed by a hypoglycaemic coma and finally death. During everyday life, the potential embarrassment that may result from hypoglycaemic symptoms is a constant source of concern and causes considerable psychological stress to many diabetics. In situations where full ability to react, motor capabilities and general awareness is crucial, like in some sports or when driving a car, hypoglycaemias may lead to potentially fatal accidents. The nocturnal sleep is a serious source of concern for many diabetics because the hypoglycaemia awareness of many diabetics is disabled or largely reduced in this time period.

In order to generally monitor correct operation of the insulin pump and to allow appropriate reaction in case of exceptional circumstances, such as hyperglycaemic or hypoglycaemic excursions, diabetics on CSII therapy need to test their glucose level at least several times a day, typically using glucose meters based on invasive (finger-prick) spot measurements of the glucose and/or, in recent times, using a Continuous Glucose Monitor (CGM), typically measuring glucose in the interstitial tissue.

While requiring considerable technical effort as well as constant awareness of the diabetic (or a person such as a relative), CSII therapy allows maintaining the diabetic's metabolism and in particular his or her glucose level in a close-to-normal range in everyday life. There is, however, a general concern with respect to the awareness of and appropriate reaction on hypoglycaemias as explained before.

To cope, among others, with such situations, closed-loop-systems (also known as Artificial Pancreas (AP)), have been under development for many years now, in which a CGM is operatively coupled to an insulin pump via a control algorithm in order to automatically ensure appropriate insulin infusion. Because of its high costs, technical complexity and safety concerns, however, no such systems are commercially available or in routine use.

With recent improvements in the development of CGM systems, however, Low Glucose Suspend (LGS) systems have become available. In such a system, an insulin pump is generally operated and infuses basal insulin like in standard CSII therapy according to a preset infusion schedule. A CGM, however, is additionally present and coupled to the control unit of the insulin pump. In case of the occurrence of a hypoglycaemia—detected by the glucose level falling below a low shutoff threshold—the pump is automatically shut off, resulting in insulin infusion being suspended, and a warning or alarm is provided. Infusion according to the schedule may be resumed automatically after a preset suspend time, of, e.g., 2 h, upon the glucose level rising above the threshold, or manually by the diabetic after resolving the situation. Such a system is disclosed in WO 2006/083831 A1, a commercial system is known as MiniMed Paradigm VEO by Medtronic MiniMed, Inc.

In practice, however, the advantages of systems as described above is limited by drawbacks that at least significantly reduce the practical value. Current LGS or similar approaches act in a static way, based on pre-programmed glucose thresholds. In order to safely prevent nocturnal hypoglycaemia, the low shutoff threshold is typically set to a comparatively high glucose level, the occurrence of which would generally not be a reason for concern as long as the diabetic is awake and conscious. A considerable number of erroneous shutoffs or "false alarms" is therefore known to occur. In addition, a fixed shutoff threshold is not considered to be appropriate in all situations. During daytime, an office worker may, for example, be willing to accept or even strive at comparatively low glucose levels in order to avoid long-term complications that are known to be associated with frequent hyperglycaemias. In a business meeting or when driving a car, she or he may whish to ensure a somewhat higher glucose level to safely avoid hypoglycaemias where—at the best—concentration, the ability to respond, and the general motor behaviour are aversively affected, while a moderate hyperglycaemia causes by far less concern when occurring occasionally and for a comparatively short time period only.

SUMMARY

The present disclosure teaches control units for pump units as used in diabetes therapy systems for CSII therapy, corresponding diabetes therapy systems and methods of operating such systems which improve the situation with respect to the handling of hypoglycaemias and can be provided based on proven and established technology and at reasonable costs that are comparable to current systems.

Disclosed is, in one aspect, a control unit for an electronically controlled pump unit, the control unit being designed to control the pump unit to infuse insulin into a diabetic's body in a substantially continuous way according to a preset infusion schedule as a function of time. In typical embodiments, the control unit is further designed to control the pump unit to additionally infuse insulin boli on demand and—in some embodiments—an overshot bolus as will be discussed below.

The pump unit may be designed according to principles that are known in the art. The pump unit may especially be designed as syringe driver unit, typically comprising an electric motor that is coupled to a linear displacement spindle. In operation, an end section of the spindle is coupled to a displaceable piston of a syringe-like insulin container. Controlled operation of the motor results in corresponding amounts of liquid insulin being displaced out of the container and being infused. Designs that may be used in the context of the present disclosure are disclosed, e.g., in the WO 2010/055504 A1, WO 01/72358 A1, WO 2009/077143 A1, or WO 00/25844 A1. Alternatively, the pump unit may be designed as disposable dosing unit as disclosed in the WO 2008/110263 A1 and the WO2010/028719 A1. The pump unit may alternatively be designed according to further principles that are known in the art for this type of application, for example as micro-membrane pump or micro peristaltic pump.

The control unit is typically based on solid-state technology, with at least part of the functionality being implemented as firmware code in one or more microcontrollers, ASICS, or the like. The control unit may further include components such as a real-time clock, static and/or dynamic memory that stores information such as the preset infusion schedule, watch dogs, power supply and power management circuitry, and the like. The control unit may further include or be coupled to a user interface and a data interface for communication with devices such as CGM systems, general glucose meters, standard computers (PCs), cell phones, and the like via wired or wireless connection. Further aspects of typical control units will be discussed below. The control unit may especially be part of a diabetes therapy system as will be discussed below in more detail, and may be realized fully or partly integral with further units or devices of such a system.

Typically, the control unit is—at least in part—realized with the pump unit in an integral way in form of a generally self-contained infusion pump device, while other parts and components of the control unit may be part of the same or a different physical device. In such an embodiment, control unit and pump unit are normally in wired or galvanic coupling. Dependent on the overall device, however, transmission of power and/or control signals as well as feedback signals may be wireless.

In accordance with an aspect of the present disclosure, the control unit includes an intervention unit. The intervention is designed to continuously evaluate a glucose indicative input for detecting an actual or expected hypoglycaemia and to execute, in response to an actual or expected hypoglycaemia, a temporary hypoglycaemia intervention. The hypoglycaemia intervention includes, for an intervention time interval, overriding the preset infusion schedule by temporarily suspending insulin infusion or temporarily reducing insulin infusion below the preset infusion schedule. Here and in the following, "intervention" generally refers to a hypoglycaemia intervention where not explicitly stated differently.

The intervention unit is designed to adapt its way of operation with respect to executing the hypoglycaemia intervention in dependence of a control signal. The control unit is designed to automatically generate the control signal as a function of time and/or based on sensor input. The control signal is separate, i.e., different and independent, from the glucose-indicative input. The control signal is typically a signal that is generated in dependence of time or is a sensor signal or derived from a sensor signal. Adaption can be carried out during continuous insulin infusion by the pump unit. The intervention unit may adapt its way of operation during regular operation, i.e., during the control unit controlling the pump unit to infusion insulin according to the preset infusion schedule.

The control unit automatically generating the control signal as a function of time and/or based on sensor input implies that the control signal is different from a static configuration parameter setting by a device user, e.g., for generally enabling/disabling the intervention unit and/or static setting of intervention parameters, such as intervention thresholds as will be further described below.

Continuously receiving and evaluating the glucose indicative input implies that these steps may be carried in a truly continuous way or in a virtually or substantially continuous way, i.e., with an interval that is short as compared to the glucose dynamics and may, e.g., be in a range up to 15 min, e.g., 1 sec, 10 sec, 30 sec, 1 min, 2 min, 2 min, 5 min, 10 min or 15 min.

Designing the intervention unit in this way allows appropriate operation in different situations and under varying conditions. As will be discussed below in the context of exemplary embodiments, such design of the intervention unit avoids or at least significantly reduces the disadvantages and drawbacks that are associated with prior art systems, such as "false alarms" that are common for the known LGS feature as discussed above.

Because the pump unit generally operates according to a preset schedule and the intervention unit only comes into action—in accordance with the control signal—in specific situations that require well-defined reactive measures, the technical complexity and risks of a closed-loop system are avoided. Furthermore, the disclosed intervention unit can, in various embodiments, be implemented with moderate firmware effort and no or little additional hardware effort in a cost-efficient way.

Interaction between the control unit as a whole and the hypoglycaemia intervention unit may generally be carried out in two alternative ways. According to the first alternative, the control unit generally controls the pump unit to infuse insulin according to the preset infusion schedule, and an intervention trigger signal or intervention trigger command is generated by the intervention unit if a hypoglycaemia intervention shall be executed. Generation of the intervention trigger signal or intervention trigger command accordingly results in overriding the preset infusion schedule. This type of embodiment has the particular characteristic of the control unit ensuring normal operation according to the preset schedule in a case of failure, e.g., of the hypoglycaemia intervention unit or of a CGM providing the blood-glucose indicative input.

According to the second alternative, the control unit generally controls the pump unit to override the preset infusion schedule by suspending insulin infusion or reducing insulin infusion below the preset infusion schedule, and an intervention suppressing signal or intervention suppressing command is generated by the intervention unit as long as no intervention shall be initiated, i.e., during regular operation. Generation of the intervention suppressing signal or intervention suppressing command accordingly results in the pump unit carrying out the infusion according to a preset infusion schedule. Upon the intervention suppressing signal or intervention suppressing command not being present, the hypoglycaemia intervention unit is automatically carried out. The intervention suppressing signal or intervention suppressing command is favourably generated continuously as long as no intervention shall be carried out. This type of embodiment has the particular characteristic of the control unit enforcing a safe state where no potentially dangerous amounts of insulin may be infused in a case of failure, e.g., of the hypoglycaemia intervention unit or of a CGM providing the blood-glucose indicative input.

The intervention unit may be designed to execute the hypoglycaemia intervention upon a glucose value of the diabetic falling below a lower intervention threshold.

Glucose values that serve as glucose indicative input for the intervention unit may be actual measurement values or signals. Alternatively, however, it may be predicted values or signals. In this case, a glucose prediction unit is present that may, e.g., be part of the control unit or a CGM. Considerable effort has been spent in developing methods and algorithms for glucose prediction or extrapolation, and a variety of methods is available that may be used in the context of the present disclosure and may be based, e.g., on linear or non-linear extrapolation. Suited algorithms are disclosed, e.g., in the WO 2006/083831 A1. In the context of the present disclosure, glucose prediction allows carrying out a hypoglycaemia intervention proactively at a point in time when the occurrence of a hypoglycaemia requiring an intervention is not yet present but can be expected to occur in the near future. An alternative to a prediction algorithm which may be computational demanding, complex and potentially susceptible to data misinterpretation, is a comparatively aggressive fixed lower intervention threshold as will be explained below may be used.

Completely suspending insulin infusion is a comparatively drastic or aggressive measure that can, however, be expected to be appropriate and effective in preventing severe hypoglycaemias, in particular during night time. It may, however, be too drastic and result in an also undesired following hyperglycaemia, depending on the circumstances and specifics of the diabetic.

Therefore, it may, in a situation of hypoglycaemia, be appropriate to only reduce insulin infusion, while avoiding a complete suspend or shutoff. The reduced insulin infusion may generally still follow the preset schedule, with the scheduled infusion rate being reduced, e.g., in a proportional way, by a reduction factor <1. The reduction factor may, for example, be 0.5 (resulting in the infused amounts being halved to 50% of the scheduled infusion rate), or 0.3 (resulting in the infused amounts being 30% of the scheduled infusion rate). A reduction factor of zero is accordingly equivalent to a full suspend or shut-off. Alternatively to a proportional reduction, the infusion rate may, for the time of the intervention, be set to a low constant value. It may, e.g., be set to a rate of 0.1 IU/h to 0.3 IU/h (International Units per hour). A reduction factor and/or a constant rate to which insulin infusion may be temporarily set may be preset configuration parameters that are typically set and tuned by a healthcare professional. Further variants that are based on a successive reduction of the insulin infusion will be explained further below.

The glucose indicative input may be a glucose value. A glucose value may be provided by a spot glucose meter that is operatively coupled to the control unit to transfer a measured glucose value to the control unit. Alternatively, glucose values may be manually entered via a user interface. In a further configuration, the glucose indicative input may be given by a glucose value that is provided by a CGM that monitors the diabetic's glucose level continuously or quasi continuously, e.g., with a measurement interval of a few minutes. While single-spot measurements may often be sufficient during daytime, continuous glucose monitoring is particular advantageous if it is desired to automatically detect a situation of actual or expected hypoglycaemia, in particular during nocturnal sleeping time, during an extended business meeting, when driving a car, or the like.

Along with or as part of the hypoglycaemia intervention, a notification or alert may be provided via an alerting unit. The alerting unit may, e.g., be or include an optical indicator such as an (O)LED or a display, an acoustic indicator such as a buzzer or loud speaker, or a tactile indicator, such as a pager vibrator. Such indicators are typically present in diabetes therapy systems and devices for alerting and alarming as well as for general user feedback purposes. Alerting may be selectively activated or deactivated and/or the type of alert may be selected by an alert control signal. An acoustic and a tactile indication may be provided during night time in order to waken the diabetic and make him or her aware of a metabolic situation that may need immediately be taken care of, such as a hypoglycaemia, while this may not be necessary and desired at daytime for a diabetic with normal hypoglycaemia awareness.

The intervention unit may be designed to terminate the hypoglycaemia intervention a given time interval after starting the hypoglycaemia intervention, or upon a glucose value of the diabetic rising above an upper intervention threshold, or upon a resuming command provided by a user.

In case of terminating the intervention a given time interval after starting the hypoglycaemia intervention, this time interval can be the intervention time interval.

After termination of the hypoglycaemia intervention, infusion according to the preset schedule may be directly resumed. Alternatively, special steps may be carried out to prevent subsequent complications resulting from the suspended or reduced infusion during the intervention time interval. Those steps may especially include the administration of an overshot bolus as will be explained further below.

A glucose value that serves as basis for terminating the hypoglycaemia intervention may be provided as glucose indicative input in the same ways as discussed above. In case a glucose value is provided as spot monitoring value, the control unit favourably includes a reminder timer that is started along with the hypoglycaemia intervention and reminds the diabetic to do a further measurement after an alerting interval of, e.g., 30 min, 45 min, or 60 min has lapsed. In dependence of the glucose value, the intervention unit may either terminate the hypoglycaemia intervention, resulting in infusion being resumed according to the preset schedule, or continue with the intervention in case the glucose value is still low. In this case, the reminder timer is favourably re-triggered with the same or a different alerting interval.

In a variant, insulin infusion according to the preset schedule is resumed upon a glucose value of the diabetic rising above an upper intervention threshold, but not before expiry of a preset minimum intervention time interval.

In case of both a lower and an upper intervention threshold being present, the upper intervention threshold may be identical to the lower threshold. Alternatively, the upper intervention threshold may be selected above the lower intervention threshold for safety reasons and to provide some hysteresis which is favourable with respect to operational stability.

The control signal may include at least one of the lower intervention threshold and the upper intervention threshold. Alternatively or additionally, the control signal may include a reduced level of insulin infusion below the preset schedule and/or the intervention time interval. As described before, a reduced level of insulin infusion may in particular be defined as reduction factor as compared to the preset schedule or as a fixed infusion rate.

All of these control signals have the result of the intervention unit operating, in dependence of the control signal, in a more conservative or more aggressive way.

In the present context, "conservative" generally means that a hypoglycaemia intervention is carried out at (comparatively) low glucose levels only, and/or that the physiological effect of a hypoglycaemia intervention is comparatively small or limited. The intervention unit may accordingly come into action and overrule the preset schedule only if a hypoglycaemia is almost certainly given or to be expected. Additionally or alternatively, the effect of the intervention may be comparatively small as compared to infusion without hypoglycaemia interventions. While "false alarms" can be safely avoided in this case, an actual moderate hypoglycaemia may not be detected in some cases.

"Aggressive" generally means that a hypoglycaemia intervention is carried out already at (comparatively) high glucose levels, and/or that the physiological effect of a hypoglycaemia intervention is comparatively large. In this case, the occurrence of actual hypoglycaemic excursions can be prevented with high certainty, while "false alarms" may be somewhat more likely to occur as compared to the "conservative case", potentially resulting in undesired hyperglycaemias.

Via the control signal, different levels of "aggressiveness" may be selected. The intervention unit may, for example, be controlled to act in a comparatively conservative way during daytime in order to prevent "false alarms", but to act more aggressively during nocturnal sleep or similar situations in order to safely prevent the occurrence of hypoglycaemic excursion in this critical phase as will be explained further below.

The intervention unit may be designed to adapt its way of operation during execution of the hypo-glycaemia intervention. Adapting the way of operation of the hypoglycaemia intervention unit may especially be carried out in dependence of the diabetic's glucose course as explained in the following.

The intervention unit may be designed, when executing the hypoglycaemia intervention, to successively reduce insulin infusion and/or, when terminating the hypoglycaemia intervention, to successively increase insulin infusion back to the preset schedule. Such successive reduction of insulin infusion when executing the hypoglycaemia intervention may, e.g., be carried out in a number of discrete reduction levels (RLs), for example RL1 reduction to 80% of preset schedule
RL2 reduction to 60% of preset schedule
RL3 reduction to 40% of preset schedule
RL4 reduction to 20% of preset schedule
RL5 reduction to 0 (corresponding to a full suspend)

Operation of such an intervention unit is further explained with reference to FIG. 5, schematically illustrating exemplary ways of operation of a control unit and an intervention unit with a number of discrete reduction levels. Curves 200, 210, illustrate a more moderate and an alternative more aggressive way of operation of the hypoglycaemia intervention unit. Curves 200, 210 show, on the vertical axis, the insulin infusion while a hypoglycaemia intervention is carried out as percentage of the infusion according to preset schedule as a function of time on the horizontal axis. The hypoglycaemia intervention begins at time $t_0$ and is terminated at time $t_1$.

Change between the individual reduction levels may be carried out in dependence of the diabetic's glucose course during the hypoglycaemia intervention. The intervention may, e.g., start with moderate level RL1. If the glucose values do not rise in the following or continues falling, a further reduction to RL2 may be carried out, and so forth. For conservative curve 200, reduction ends at a minimum reduction level RL3. Alternatively, stepwise reduction may be continued, to any other minimum reduction level, potentially up to a potential full suspend. A number of glucose thresholds GT1 . . . GT5 (not shown in FIG. 5), corresponding to the above-given exemplary reduction levels RL1 . . . RL5, may be defined and stored by the control unit or the intervention unit, with GT1 as the highest glucose value corresponding to the lower intervention threshold at which the hypoglycaemia intervention is carried out. While the succession between the reduction levels is shown with equal time intervals, they will, for this type of embodiment, typically not be equal but depend on the diabetic's glucose course during the hypoglycaemia intervention. Additionally, a switch to reduction levels RL2 and/or reduction level RL3 may not occur if the diabetic's glucose value starts rising sufficiently fast.

The more aggressive way of operation of the hypoglycaemia intervention unit, illustrated by curve 210, differs from the more moderate behaviour mainly by a steeper decrease of the infusion and a lower minimum infusion level, in curve 210 shown as full suspend of infusion to reduction level RL5.

A successive increase of the infusion, thus returning to the preset schedule, may be carried out additionally or alternatively in an analogue way, as illustrated the rising edges of curves 200, 210. In a variant, insulin infusion is reduced to a minimum level or fully suspended right at the beginning of the hypoglycaemia intervention, while resuming infusion according to the preset schedule is carried out successively, using, e.g., the above-given levels. For such an embodiment, the falling left edge of curves 200, 210 would be vertical. Likewise, it is possible to reduce the infusion successively and to resume infusion according to the preset schedule directly without intermediate steps. For such an embodiment, the rising right edge of curves 200, 210 would be vertical.

Alternatively to a successive reduction and/or resuming of insulin infusion in dependence of the diabetic's glucose course, the control unit may be designed to store a preset successive reduction regime and/or a preset successive resuming regime and to execute a hypoglycaemia intervention according to the preset regime. Such a regime may, e.g., include a stepwise reduction of the infusion with the above-given reduction levels according to the left falling edges of curves 200, 210. The time interval between the single reduction steps may, e.g., be 15 min each. Once the beginning of a hypoglycaemia intervention has started, successive reduction to the minimum level or full suspense is then carried out according to the preset reduction regime, independent of the course of the diabetic's glucose value.

Resuming may be carried out in a single step or according to a preset successive resuming regime. For an embodiment where the duration of the intervention time interval is given, a hypoglycaemia intervention may, from beginning to end, accordingly be defined by a reduction-vs-time curve, like curves 200, 210.

The intervention unit may be designed to determine a level of reduction of insulin infusion below the preset schedule and/or the intervention time interval in dependence of the blood-glucose indicative input. The blood indicative input may, e.g., be a glucose level or a glucose trend at the beginning of the hypoglycaemia intervention. This type of embodiment allows to automatically adapt the aggressiveness level of the hypoglycaemia intervention in dependence of the glucose.

In an example, a reduction to above-defined level RL1 is carried out for a glucose value below glucose threshold GT1 as explained above or a glucose trend indication that the glucose value will slowly fall below this threshold. For a rapid glucose decrease, indicating, e.g., that the glucose value has, starting from a value above GT1, rapidly fallen or will rapidly fall below GT4 or GT5, the hypoglycaemia intervention may accordingly be carried out with a reduction to RL4 or RL5.

The control unit may include a clock unit and may be configured to generate the control signal in dependence of a time of day.

The control signal may include an enablement signal and the intervention unit may be designed to selectively enable or disable execution of the hypoglycaemia intervention in dependence of the enablement signal. Disabling the hypoglycaemia intervention is a limit case of "conservative" behaviour and results in the control unit and the pump unit to temporarily operate in the same way as if no intervention unit was present. Alternatively to providing a dedicated enablement signal, it is, in some embodiments, generally possible to temporarily disable or deactivate the intervention unit by setting a lower intervention threshold that is higher than a glucose value that may be expected to occur in practice.

In embodiments where the intervention unit is designed to execute, besides the hypoglycaemia intervention, one or more further intervention, such as a hyperglycaemia intervention, or in case more than one intervention unit is present in parallel, the same enablement signal may be used for enabling and disabling the execution of the hypoglycaemia intervention and further interventions. Alternatively, separate enablement signals may be foreseen.

In embodiments involving a time-of-day dependent enablement signal, executing the hypoglycaemia intervention may be automatically enabled during nighttimes and may be disabled, i.e., deactivated, during daytime where the diabetic would normally become aware of a situation requiring an intervention and the optional accompanying alerts would be disturbing, e.g., during a business meeting or in a public environment.

Time-of-day dependent control parameters that are provided as control signal to the intervention unit may be preset and stored as control parameter profile in typically non-volatile memory, similar to the basal infusion schedule. Different control signal profiles may further be present for different days of the week, e.g., for working days and weekends. With respect to weekends, it may, e.g., be considered that the diabetic may have the habit to take a nap after lunch that should be dealt with in the same ways a nocturnal sleep.

The control unit may include or may be designed to operatively couple to a physical activity sensor—in particular one or more of an accelerometer, a pedometer, a pulse meter, an oxymeter, a breath sensor, body temperature sensors, hart rate sensors, ventilation rate sensors, amount of sweat and blood oxygen saturation sensors, EEG sensors and ECG sensors—and may be designed to generate the control signal in dependence of physical activity of the diabetic.

The control unit may be especially be designed to enable the execution of the hypoglycaemia intervention at high physical activity, in particular upon the physical activity sensor indicating sportive activity or exercise of the diabetic.

Periods of increased physical activity, such as sports or exercise, are particularly critical with respect to the occurrence of hypoglycaemias because of the increased energy consumption of the body, which causes, for diabetics, an increased hypoglycaemic risk. At the same time, the hypoglycaemia awareness is often decreased. Controlling the intervention unit in dependence of physical activity allows preventing hypoglycaemias, e.g., by setting an appropriate lower intervention threshold, without temporarily decreasing the basal administration or suspending insulin administration manually as precautious measure, which is typically done according to the state of the art in an ad-hoc and often inappropriate way. However, a temporary reduction of the infusion may be carried out in addition. State-of-the art insulin infusion devices typically allow such a reduction on request via user input.

Physical activity sensors may be an integral and dedicated part of the control unit or an overall diabetes therapy system. They may, however, fully or partly, also be realized by commercial standard devices such as standard pulse meters and standard pedometers that are carried by many people during everyday life to monitor their health state and energy consumption, or are especially carried for training or exercise and may also be part of everyday electronic devices such as smart phones. Those devices may include an RF communication interface, such as a Bluetooth/Bluetooth Low energy interface, that may favourably be used for operatively coupling to the control unit. Those devices often have a wrist-watch like design, may be carried in a pocket, worn as necklace or may—e.g., in case of pedometers—be included in functional clothing, sneakers, or the like.

The control unit may include or be designed to operatively couple to a fasting period sensor, the fasting period sensor being designed to determine a fasting period measure, indicating a started or anticipated fasting period. The control unit may further be designed to generate the control signal in dependence of the fasting period measure.

In the present context, the phrase "fasting period" refers to a period where the diabetic does not consume significant amounts of therapy-relevant food, in particular carbohydrates, for a prolonged time interval of typically a number of hours. In particular, the nocturnal sleep is considered as fasting period. The fasting period sensor may, however, also be used to indicate shorter periods such as a nap and the same procedures may be followed.

As discussed above, nocturnal hypoglycaemias are a source of particular concern for many diabetics and/or partners, parents, etc. and cause, in some cases, severe psychological stress. In case an execution of the hypoglycaemia intervention is normally disabled during daytime, the control signal may enable the execution for the nocturnal sleeping period. In case executing the hypoglycaemia intervention are generally enabled, the control signal may set different intervention thresholds for the night, in particular a somewhat higher value for the lower intervention threshold as compared to daytime, in order to safely prevent nocturnal hypoglycaemic excursions.

The control unit may be designed to enable execution of the hypoglycaemia intervention upon the fasting period measure indicating that the diabetic has fallen asleep, has gone to bed, or can be expected to fall asleep or go to bed soon.

A fasting period sensor does not necessarily provide a measure that is necessarily connected with the diabetic falling or having fallen asleep in a causal nexus. It may also be a measure that is indicative for and correlated with the diabetic's intention to go to bed soon, such as the presence in the bedroom, laying in the bed, etc.

A fasting period sensor may include one or more of a geolocation sensor, an accelerometer, a pulse meter, a single or a plurality of position transducers carried by or attached to the diabetic, and a single or a plurality of contact sensors integrated in the diabetic's bed or mattress. The fasting period sensor may at the same time be a physical activity sensor as discussed above and may be realized in the same way.

A geolocation sensor, e.g., in form of a GPS sensor, may be present to verify that the diabetic is at a place where it can be assumed that he or she will go to bed soon. Position sensors that are carried at the diabetic's body may be used to determine if the diabetic is in a substantially horizontal, i.e., lying position. Contact sensors in diabetic's bed or mattress provide an indication whether the diabetic actually is in bed.

The EP 1762259 A1 discloses further sensors that may serve as fasting period sensor in the present context, such as ambient light sensors. The EP 1762259 A1 further discloses the use of a manually operated "going-to-bed" button that is operated by a diabetic substantially at the time of going to bed. Also such a button may serve as fasting period sensor in the present context. Further sensors may be used that are mentioned above in the context of exercise or sportive activity.

While a single fasting period sensor may be sufficient under some circumstances, it may be favourable to rely on a fusion of more then one fasting period sensor. For example, a combination of a geolocation sensor and contact sensors in the mattress may be used.

The control unit may further be designed to evaluate a time of day signal that is provided by a clock unit and may be configured to generate the control signal as a combination of a time of day signal in combination with signals that are provided by one or more fasting period sensors. The control unit may especially be designed to evaluate signals as provided by fasting period sensors only if a further condition with respect to the time of day is met.

The control unit may, for example, be designed to enable an execution of the hypoglycaemia intervention if a preset going-to-bed time has been passed and the one or more fasting period sensor(s), e.g., a geolocation sensor, indicate that the diabetic actually is gone to bed, has gone to bed, is asleep, or will do so soon. If the time of day criterion is not met, the intervention unit may be disabled or active with more conservative setting as discussed above.

While requiring some additional hardware and firmware effort as compared to a pure clock-controlled generation of the control signal as described above in the context of a further embodiment, control of the intervention unit is more accurate for those embodiments that include a fasting period sensor.

The control unit may include or may be designed to operatively couple to a continuous glucose monitor (CGM), the CGM providing the blood-glucose indicative input.

The control unit may be designed to determine an overshot bolus and a compensation rate based on an amount of insulin that would be infused in accordance with the preset schedule within a compensation time interval following the hypoglycaemia intervention. The control unit may further be designed, following the intervention, to control the pump unit to infuse the overshot bolus and to control, following the infusion of the overshot bolus, the pump unit to infuse insulin temporary at the compensation rate for the compensation time period. In some of those embodiments, the control unit is designed to determine the overshot bolus and the compensation rate such that the total of the overshot bolus and the amount of insulin that is administered in the compensation time interval at the compensation rate sum up to the amount to the amount of insulin that would be administered within the compensation time interval in accordance with the preset schedule. In other words, the amount of insulin that is actually infused in the compensation time interval and the overshot bolus add up to the infusion amount in the compensation time period according to the preset schedule. Alternatively, however, the total may be larger or smaller. The compensation rate may be a fixed or flat rate or may generally follow the course of the preset schedule with some reduction.

While it is appropriate—in response to a detected actual or predicted hypoglycaemia, to temporarily suspend or reduce insulin infusion, it is known in case of a suspension or reduction for a prolonged time period, exceeding, e.g., 30 min o 1 h, a lack of insulin may occur at the end of the intervention, resulting in a following undesired hyperglycaemia. Providing, following the intervention, an overshot bolus according to this type of embodiment compensates for this lack of insulin. Reducing the scheduled infusion for a limited compensation time period prevents the overshot bolus from resulting in a further following hypoglycaemia. The control unit may be designed such that the steps of infusing an overshot bolus and following infusion at a compensation rate are carried out if the duration of the hypoglycaemia intervention exceeds a time period of, e.g., 30 min or 1 h, defined, e.g., as preset configuration parameter. The compensation time period may also be a preset parameter and be in the range, of, e.g., 1 h or 2 h.

The intervention unit may be designed to execute, in case of an actual or expected hypoglycaemia of the diabetic, a number of alternative hypoglycaemia handling routines, wherein at least one of the number of alternative hypoglycaemia handling routines includes executing hypoglycaemia intervention. This type of embodiment increases the flexibility for reacting on an actual or expected hypoglycaemia in a way that is both appropriate and acceptable for the diabetic in different situations. An alternative to the hypoglycaemia intervention as discussed so far may, e.g., be to propose the diabetic to consume an appropriate, typically calculated, amount of fast-acting carbohydrates, either without or with less temporary reduction of the infusion. Upon detection of an actual or expected hypoglycaemia, the diabetic may be provided with these alternative options and select whatever is appropriate in the specific situation. In some embodiments, the control unit may be designed to select a hypoglycaemia handling routine based, fully or partly, on the control signal. For example, the diabetic may be provided with the options for either executing the hypoglycaemia intervention or consuming carbohydrates during daytime while the hypoglycaemia intervention may in any case be executed in the nocturnal fasting period. In further embodiments, a hypoglycaemia handling strategy may be selected in dependence of the severity of an actual or expected hypoglycaemia. For example, the hypoglycaemia intervention may be executed in case of a moderate hypoglycaemia and the hypoglycaemia intervention may be executed together with a proposal for consuming fast-acting carbohydrates, such as glucose, in a more severe case.

The intervention unit may be designed to execute, in response to an actual or predicted hyperglycaemia of the diabetic, a hyperglycaemia intervention, the hyperglycaemia intervention including controlling the pump unit to infuse a correction bolus.

Under most circumstances, administration of a correction bolus is an appropriate measure in case of a hyperglycaemia, the correction bolus being computed to lower the glucose level to a target level or target range. A number of algorithms are known in the art which may differ with respect to some computational details and with respect to considered additional influence factors, but are generally based on the amount by which the glucose value should be lowered and the diabetic's individual insulin sensitivity, i.e., the effect of a given insulin dose on the glucose level. Under certain circumstances, however, a temporary reduction or suspension of the insulin infusion and/or a consumption of additional carbohydrates may be appropriate rather than the infusion of a correction bolus, despite a currently raised glucose value. This aspects will be discussed in more detail below in the context of exemplary embodiments.

Disclosed is, in a further aspect, a diabetes therapy system, including an pump unit, the pump unit being designed to be carried by a diabetic attached to his or her body or in proximity to his or her body substantially continuously and concealed from view, and a control unit as generally disclosed above and further below in the context of exemplary embodiments. The control unit of the diabetes therapy system is or is designed to operatively couple to the pump unit to control operation of the pump unit. The control unit may be realized in form of a compact single device, optionally together with further functional units such as a CGM. Alternatively, the diabetes therapy system may be made of a number of distinct an physically separate units with operative coupling.

The diabetes therapy system may include a continuous glucose monitor (CGM). As discussed above, the CGM may operatively couple to the intervention unit to provide the control signal to the intervention unit.

According to a still further aspect, the present disclosure is directed towards a method for controlling a pump unit to infuse insulin into a diabetic's body in a substantially continuous way according to a preset infusion schedule as a function of time.

The method includes executing a hypoglycaemia interventions under control of an intervention unit. The intervention may include detecting or an actual or expected hypoglycaemia of the diabetic and carrying out, in response to the actual or expected hypoglycaemia, a hypoglycaemia intervention. The hypoglycaemia intervention includes overriding, in response to the detected or predicted hypoglycaemia, the preset infusion schedule by temporarily suspending insulin infusion or by temporarily reducing insulin infusion below the preset schedule. The method further includes automatically generating a control signal as a function of time and/or based on sensor input and adapting the way of operation of the intervention unit with respect to the hypoglycaemia intervention in dependence of the control signal.

The method for controlling a pump unit may especially be carried out by a control unit including an intervention unit as generally discussed above as well as further below in the context of exemplary embodiments. In this description, some aspects of the present disclosure are given with main reference to the method while others are given mainly with reference to structural units or hardware units, such as control units and diabetes therapy systems as best suited for a clear and concise presentation. It shall be understood, however, that embodiments of hardware units at the same time define corresponding method embodiments and vice versa.

According to a still further aspect, the present disclosure is directed to a computer program product storing executable code as well as towards a tangible computer-readable medium storing the code. The code, when executed, implements functionally of a controller unit including an intervention unit and/or executes a method as generally discussed above and further below in the context of exemplary embodiments.

The above-given disclosure as well as the discussion of exemplary embodiments further below includes a number of aspects for control units including an intervention unit that do not necessarily rely on the presence of a control signal as discussed above.

In this respect, disclosed is a control unit for an electronically controlled pump unit, the control unit being designed to control the pump unit to infuse insulin into a diabetic's body in a substantially continuous way according to a preset infusion schedule as a function of time, the control unit including an intervention unit, the intervention unit being designed to continuously evaluate a blood-glucose indicative input for detecting an actual or expected hypoglycaemia and to execute, in response to an actual or expected hypoglycaemia, a temporary hypoglycaemia intervention, the hypoglycaemia intervention including, for an intervention time interval, overriding the preset infusion schedule by temporarily suspending insulin infusion or temporarily reducing insulin infusion below the preset infusion schedule.

The intervention unit is designed
  to adapt its way of operation during execution of the hypoglycaemia intervention, and/or
  when executing the hypoglycaemia intervention, to successively reduce insulin infusion and/or, when terminating the hypoglycaemia intervention, to successively resume insulin infusion back to the preset schedule, and/or
to determine a level of reduction of insulin infusion below the preset schedule and/or the intervention time interval in dependence of the blood-glucose indicative input.

Additionally or alternatively, the control unit may be designed to generally control the pump unit to override the preset infusion schedule by suspending insulin infusion or reducing insulin infusion below the preset infusion schedule, and the intervention unit may designed to generate an intervention suppressing signal or intervention suppressing command as long as no intervention shall be initiated. The disclosure of any of such control units implicitly also discloses a corresponding method for controlling a pump unit, the method being carried out by operating the control unit.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1 shows an exemplary embodiment of a diabetes therapy system in a schematic structural view.

FIGS. 2a, 2b show exemplary control signals.

DESCRIPTION

Figure 4:
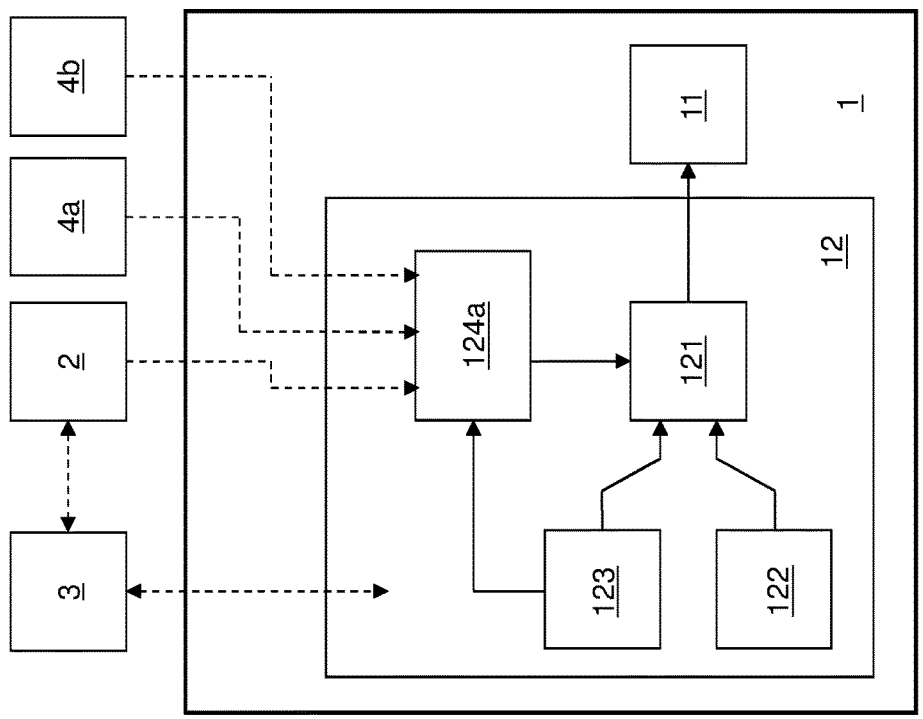
FIG. 4 shows a further exemplary embodiment of a diabetes therapy device in a schematic structural view.

The embodiments described below are not intended to be exhaustive or to limit the invention to the precise forms disclosed in the following description. Rather, the embodiments are chosen and described so that others skilled in the art may appreciate and understand the principles and practices of this disclosure.

The exemplary diabetes therapy system of FIG. 1 includes, in an operational state, a compact and self-contained infusion pump device 1. Infusion pump device 1 includes a pump unit 11 and a control unit 12. Pump unit 11 is in the following exemplarily considered as being a syringe driver pump with a motor-driven threaded spindle. Pump unit 11 may, however, alternatively be designed according to another principle as discussed above.

Control unit 12 is realized by microcontroller-based solid state circuitry as generally known in the art. Control unit 12 includes pump driver 121, memory 122, clock unit 123, and intervention unit 124. Memory 122 is non-volatile and stores a circadian infusion schedule. During normal operation where no intervention is carried out, a time-of-day signal that is provided by clock unit 123 and the infusion schedule as stored in memory 122 are fed into pump driver 121 and pump driver 121 drives and operates pump unit 11 in accordance with the infusion schedule and the time of day.

The time of day signal is further fed from clock unit 123 into intervention unit 124 as control signal, resulting in operation of intervention unit 124 to adapt and vary its behaviour in accordance with the time of day, as will be discussed below in more detail.

The exemplary diabetes therapy system of FIG. 1 further includes a continuous glucose monitor (CGM) 2 that is carried by the diabetic and determines its glucose level in a continuous or quasi continuous way. CGM 2 is operatively coupled to intervention unit 124 for transmitting and feeding an output signal into intervention unit 124 as glucose indicative input. While a number of technologies are available for establishing the operative coupling, such as a wired connection, an infra red (IR) connection, a wireless short range radio frequency (RF) link is assumed in the following, the RF link being realized, e.g., according to the Bluetooth standard. CGM 2 may directly transmit the continuous measured glucose date. Alternatively, however, some degree of processing may be carried out in CGM 2, such as noise reduction, peak detection, trend analysis, etc.

Like in the following discussion of further exemplary embodiments, FIG. 1 only shows those structural and functional features as well as their interaction that are of particular relevance in the context of the present disclosure, without excluding the presence of further features, components and interactions. Infusion pump device 1 may, e.g., include a power supply, such as rechargeable and/or non-rechargeable batteries, a user interface, wired and/or wireless communication interfaces, power management circuitry, watchdog and further safety circuitry, and the like.

As discussed above in context of the general disclosure, a (not shown) alerting unit may be present and operatively coupled to intervention unit 124 to provide a user alert in case of an intervention. The exemplary system of FIG. 1 further includes an optional remote control unit 3 that is operatively coupled to control unit 12 of infusion pump device 1, favourably via a wireless communication interface, based, e.g., on the Bluetooth standard or the like. Remote control unit 3 includes a user interface with, e.g., some or all of a display, an audio altering unit, a tactile alerting unit, push buttons, switches, a touch screen, and the like. Remote control unit 3 may be used by the diabetic for controlling operation of the diabetes therapy system in daily use. Remote control unit 3 may further include advanced functions for determining insulin boli to be infused in the context of food intake and/or for lowering raised glucose values, and may further include functionality such as therapy statistics. Remote control unit 3 may further serve as relay to couple infusion pump device 1 and/or CGM 2 to a remote computer, e.g., for configuration and/or data archiving purposes. Embodiments of remote control unit 3 may further include a glucose meter. A remote control unit 3 may, in summary, offer functionality as known, e.g., from ACCU-CHEK® Aviva Combo devices as provided by Roche Diagnostics, or as disclosed in the EP 01920640 A1.

As further indicated in FIG. 1, remote control unit 3 may operatively couple to CGM 2. In such an embodiment, remote control unit 3 may be designed to receive and evaluate glucose data from CGM 2 substantially continuously, in given time intervals of, e.g., some minutes up to 1 h and/or on request. Remote control unit 3 may store those data for diary keeping purposes and may display those data as well as trends and/or warnings that are derived from those data, e.g., in form of a glucose versus time curve on a display of remote control unit 3. A spot glucose meter provided in remote control unit 3 may further generate calibration data for CGM 2.

In embodiments where remote control unit 3 is present, it is generally possible to operatively couple CGM 2 to control unit 12 via remote control unit 3 as relay. In this case, however, executing an intervention as discussed below requires remote control unit 3 to be generally present and operating. Therefore, a direct and independent operatively coupling may be provided between CGM 2 and control unit 12 to provide the glucose indicative input to interaction unit 124, whether or not an operatively coupling between CGM 2 and remote control unit 3 is provided, as indicated in FIG. 1.

In FIG. 1, like in FIG. 4 discussed further below, solid lines between functional units indicate a typically galvanic or wired coupling, with the corresponding connected components being typically realized in a common physical unit. Dashed lines indicate wireless operatively coupling between typically separate and remote physical units. In alternative embodiments, however, the design as wired or wireless coupling may be different, in dependence of the overall architecture. They are therefore not to be understood as limiting.

It is further to be understood that the shown differentiation between individual functional units is mainly made to clarify the operational relation and interaction between functional units. In practice, some of those units may be realized by a single physical component, such as a microcontroller, or distributed between a number of physical components. For example, memory 122 and clock unit 123 may be realized together with intervention unit 124 in a single microcontroller generally representing control unit 12. Typically, all or some of the functionality is implemented as firmware code in a single or a number of microcontrollers, ASICS, and the like.

FIG. 2a illustrates an exemplary control signal for intervention unit 124. In this embodiment, the control signal is given by a binary signal A as enablement signal. Logic "1" indicates that execution of the hypoglycaemia intervention is enabled while logic "0" indicates that execution of the intervention is disabled. In FIG. 2a, signal "A" is shown as function of time t for a circadian cycle from midnight to midnight. Execution of the hypoglycaemia intervention is enabled from about 23:00 to 6:00 and disabled otherwise. The time where execution is enabled corresponds to the diabetic's typical fasting periods during nocturnal sleep while the time where execution is corresponds to the diabetic's daytime. The times of day where interventions are enabled and disabled, respectively, are favourably therapy parameters that are stored in non-volatile memory of control unit 12, for example in memory 122.

As discussed above in the context of the general description, the hypoglycaemia intervention may either cause a complete temporary suspend of insulin infusion by pump unit 11 or a temporary infusion at reduced rate below the preset infusion schedule as stored in memory 122. For the embodiment of FIG. 2a, the intervention is executed upon the diabetic's glucose value falling a lower intervention threshold of, e.g., 70 mg/dl, the low intervention threshold being a pre-set parameter that is stored in non-volatile memory of control unit 12. As discussed above in the context of the general description, the intervention may be terminated and infusion according to the preset schedule may be resumed a given intervention time interval after beginning of the intervention, or upon the glucose value rising above an upper intervention threshold, with the intervention time interval or the upper intervention threshold being stored parameters.

FIG. 2b schematically illustrates the course of a circadian control signal for an alternative embodiment of intervention unit 124. For this embodiment, executing the hypoglycaemia intervention is enabled at all times of the day. The control signal, however, varies the lower intervention threshold in dependence of the time of day, as reflected by the course of signal "L". From about 23:00 to 6:00, the lower intervention threshold is set to 70 mg/dl, and is set to 50 mg/dl for the rest of the day where the diabetic is awake. From 6:00 to 23:00, the hypoglycaemia intervention is accordingly carried out upon the glucose value falling below 50 mg/dl, while it is carried out upon the glucose value falling below 70 mg/dl from 23:00 to 6:00, resulting in a more aggressive nocturnal operation of intervention unit 124 as compared to a more conservative operation for the rest of the day.

In addition to the lower intervention threshold, FIG. 2b shows a time varying upper intervention threshold for terminating the hypoglycaemia intervention as further component of the control signal, reflected by the course of signal "U". In the example, the upper intervention threshold is set to 120 mg/dl for the nocturnal time from 23:00 to 6:00 and to 90 mg/dl for the rest of the day. Alternatively to a time-dependent upper intervention threshold, a time variable lower intervention threshold may be used in combination with a preset intervention time period.

Alternatively to clock unit 123 providing a signal of the form as shown in FIG. 2a, 2b to intervention unit 124, clock unit 123 may provide the time of day signal as such to intervention unit 124, with a signal as shown in FIG. 2a, 2b being generated internally by intervention unit 124.

Figure 3:
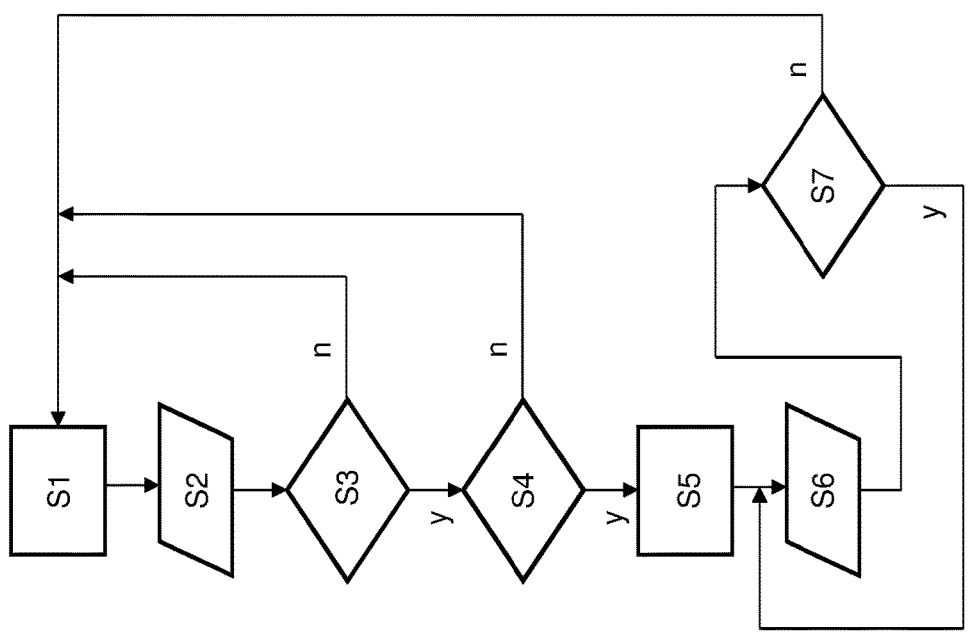
FIG. 3 shows an exemplary operational flow for a hypoglycaemia intervention in a system according to FIG. 1.

FIG. 3 illustrates the major steps of an operational flow for an embodiment in accordance with FIG. 1, with an enablement signal as shown in FIG. 2a. In this example, preset lower and upper intervention thresholds are assumed. Like in further examples that will be discussed below, control of the single steps is carried out under control of control unit 12.

In step S1, pump unit 11 is controlled in accordance with the schedule as stored in memory 122 and no hypoglycaemia intervention is executed. Unless an intervention is carried out and infusion according to the preset schedule is overruled, infusion according to the preset schedule is assumed to continue during the following steps. In step S2, a glucose value is received from CGM 2 as glucose indicative input. In step S3, the received glucose value is evaluated by determining whether the value received in step S2 is below the lower intervention threshold. If this is not the case, infusion according to the preset schedule in step S1 is continued.

If the glucose value is below the lower intervention threshold, the enablement signal is evaluated step S4. That is, it is determined whether or not execution of the hypoglycaemia intervention is enabled. If execution is disabled, infusion according to the preset schedule in step S1 is continued.

Figure 5:
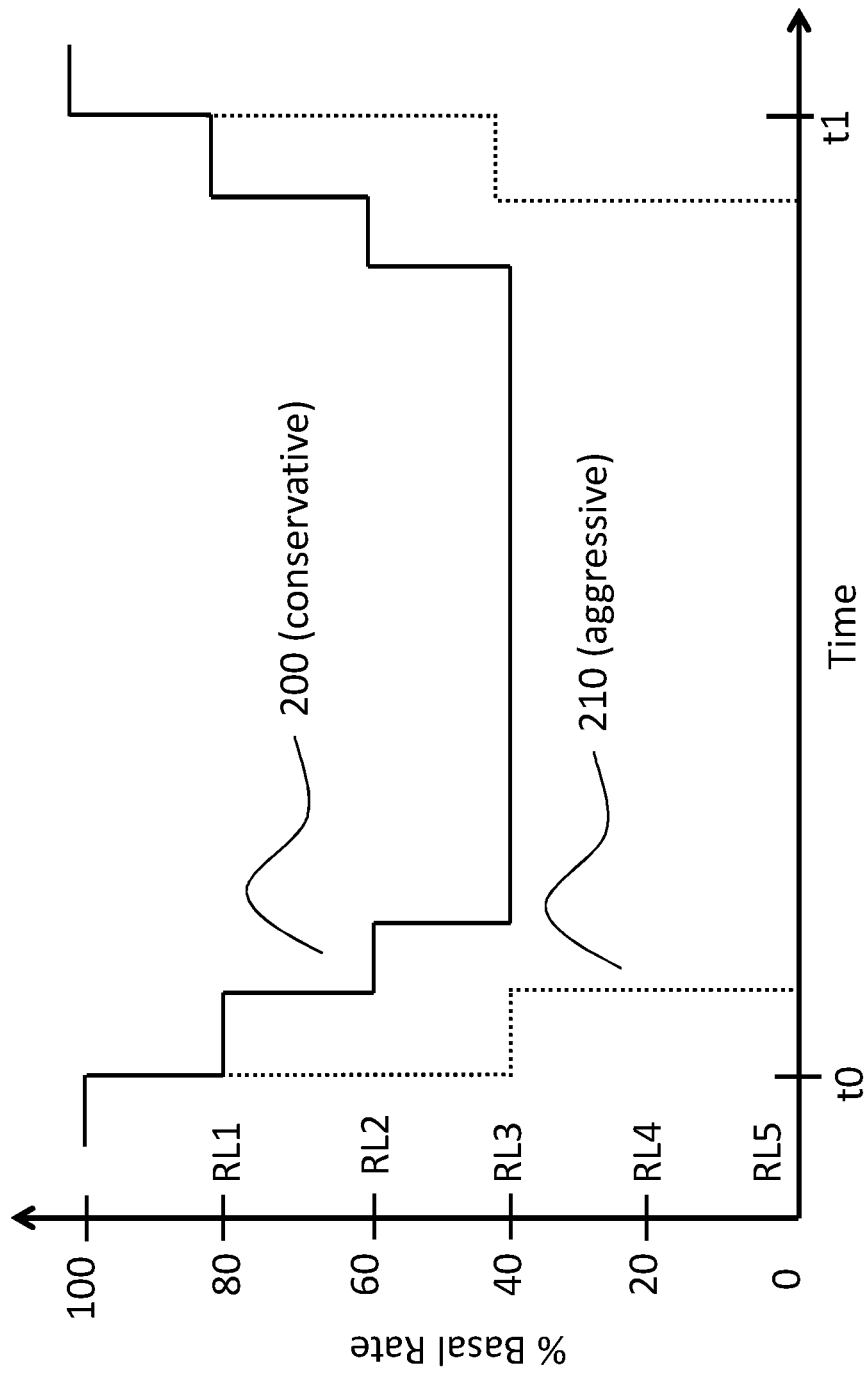
FIG. 5 illustrates exemplary ways of operation of control units in accordance with the present disclosure (discussed before).

If execution of the hypoglycaemia intervention is enabled, intervention unit 124 starts overriding the administration schedule in step S5. In this description, it is assumed that hypoglycaemia intervention unit 124 is designed to either temporarily suspend insulin infusion or to reduce infusion in a single step. In variants, however, intervention unit 124 may be designed to successively reduce the insulin infusion according to a preset regime or in dependence of the glucose course, as discussed above in the general description in context of FIG. 5. Likewise, when subsequently resuming infusion (step S6 as discussed below), resuming is exemplarily assumed to be done in a single step. Alternatively, resuming infusion may be carried out successively. Successive reduction or resuming of the insulin delivery may, e.g., be carried out in a number of discrete steps or in a continuous way.

In step S6, a next glucose value is received from CGM 2. In step S7, the glucose value is evaluated by determining whether the glucose value received in step S6 is below the upper intervention threshold. If this is not the case, i.e., if the glucose value has, between step S2 and step S6, raised above the upper intervention threshold, the hypoglycaemia intervention is terminated and infusion according to the preset schedule in step S1 is resumed. Otherwise, the intervention is continued and a next glucose value is received in step S6.

While FIG. 3 illustrates a basic exemplary operational flow, a number of modifications and alternative ways and orders of carrying out the single steps are well possible. In the embodiment of FIG. 3, for example, an intervention, once started in step S5, is continued until it is determined in step S7 that the glucose value has risen above the upper intervention threshold, independent of the further course of the enablement signal. By evaluating the enablement signal during the intervention it is alternatively possible to terminate the intervention upon the execution of interventions being disabled via the enablement signal.

As described above, a user alert may further be provided by activating an alerting unit along with starting the hypoglycaemia intervention in step S5.

In further variants, a user input is requested as confirmation before starting an intervention in step S5 and/or terminating it in step S7. In further variants, after beginning the hypoglycaemia intervention in step S5, a delay may be provided to ensure that the intervention, once started, is executed at least for a minimum intervention time period. Similarly, the hypoglycaemia intervention may only be started if the glucose value stays below the lower intervention threshold for a preset minimum time period and/or may be terminated only if it continuously stays above the upper intervention threshold for a preset minimum time period.

Intervention unit 124 may, fully or partly, be realized integral with a control unit of CGM 2. In particular, comparing a measured or predicted glucose value with a lower and/or upper intervention threshold may be carried out in CGM 2 and a trigger signal may be transmitted from CGM 2 to infusion pump device 1 only if the lower or upper intervention thresholds are fallen below or raised beyond, respectively.

In the example of FIG. 3, glucose values are received and evaluated substantially continuously in steps S3, S6, independent form the enablement signal. This is generally considered favourable since diabetics carrying a CGM typically want to continuously track their glucose level. By exchanging step S2 and Step S3, however, it is also possible to receive and evaluate data from CGM 2 only if execution of the hypoglycaemia intervention is enabled.

FIG. 4 shows a further exemplary embodiment of a diabetes therapy system in a schematic functional view. The general design and operation is similar to the embodiment as shown in FIG. 1, with the following discussion being focussed on differentiating aspects. While the control signal for intervention unit 124 in FIG. 1 is given by a time of day signal that is provided by clock unit 123, intervention unit 124a of FIG. 4 receives and evaluates additional input from sensors 4a, 4b.

For the moment, sensors 4a, 4b are considered as fasting period sensors as discussed above in the general discussion of the disclosure. Without excluding other types of sensors, sensor 4a is in the following exemplarily assumed as GPS sensor as an embodiment of a geolocation sensor, and sensor 4b is assumed as a single or a plurality of contact sensors that are integrated in the diabetic's mattress. Sensors 4a, 4b, may be operatively coupled to control unit 12 via any short range communication link, e.g., Bluetooth or Bluetooth Low Energy, as discussed above in the context of CGM 2. In some embodiments, GPS receiver 4a may also be realized integral with infusion pump device 1 or remote control unit 3. GPS receiver 4a may also be integral with a smart phone or the like. Generally, GPS sensor 4a may be integral with any device that is carried by the patient substantially continuously, such that the position of GPS sensor 4a can be assumed to also indicate the position of the diabetic.

Intervention unit 124a of the embodiment shown in FIG. 4 may generally be designed and operate similar to intervention unit 124 of the previously discussed embodiment, but differs with respect to the received control signal and its evaluation. Intervention unit 124a combines the individual inputs that are received from clock unit 123, as well as from sensors 4a, 4b, and evaluates them, in combination, as control signal.

In an embodiment, inputs received from clock unit 123 and from sensors 4a, 4b each define a binary input, with a combined input being given by a logic AND combination of the individual inputs. Intervention unit 124a may, for example, consider the beginning of a fasting period of the diabetic if the time of day is beyond a preset going-to-bed time (input received from clock unit 123), the diabetic is in the bedroom (input received from GPS sensor 4a), and the diabetic's bed is weight-loaded to or beyond a given threshold (input received from contact sensor(s) 4b). With respect to the diabetic getting up, thereby indicating an end of the fasting period, a similar binary logic may be used. The diabetic may, for example, be considered as having got up if the time of day is beyond a preset getting-up time, his or her position is outside the bedroom and the mattress is not further loaded beyond the threshold.

The operational flow may generally be the same as shown in FIG. 3 as discussed above, with the deviating handling of the control signal being reflected in step S4.

For both the embodiment of FIG. 1 as well as the embodiment of FIG. 4, additional user confirmations may be requested by the diabetic. That is, when the time of day and/or sensor signals indicate a beginning or an ending of the fasting period, he or she may be requested confirm this fact, and intervention unit 124a may proceed with the following steps only if such confirmation is provided.

The variants and additions that may be made to the embodiment of FIG. 1 may also be made to the embodiment of FIG. 4. Furthermore, only a single fasting period sensor may be present or more that the above-mentioned two sensors 4a, 4b may be present and evaluated by intervention unit 124a. In a further somewhat less complex embodiment, sensors 4a, 4b are replaced by a "going to bed" button and a "getting up" button, as discussed above in context of the general disclosure. In a further variant, no control signal is provided to intervention unit 124a from clock unit 123, but control of the hypoglycaemia intervention exclusively relies on control signal as provided by sensors 4a, 4b. It shall be noted that—in the ideal case of the diabetic following an identical daily routine with little day-to-day variability and disregarding the possibility of sensors 4a/4b providing wrong or misleading signals as will be discussed below—the control signal provided by clock unit 123 and by either of sensors 4a, 4b is redundant. Therefore, it is generally possible to only rely on either or both of sensors 4a, 4b without evaluating the time of day.

In further embodiments, different logics may be used for the sensor evaluation. For example, the beginning of a fasting period may be assumed when indicated by at least two of the three criteria time of day, GPS position and mattress load. Similarly, additional intelligence may be added to the evaluation of sensors 4a, 4b. For example, an indication provided by either of sensors 4a, 4b, indicating the beginning of a fasting period, is considered to be given if it occurs at or after the preset going-to-bed time but may be disregarded if already present for some time. For example, if GPS receiver 4a is included in a smart phone, the diabetic may have placed or forgotten it on a bedside cabinet during the day, resulting in GPS receiver 4a wrongly indicating a position in the bedroom. Similarly, a static load may be present on the diabetic's bed or mattress, resulting in contact sensor(s) 4b wrongly indicating the diabetic lying in bed. Additionally or alternatively, control unit 12 may consider the duration of an indication. For example, a diabetic may enter the bedroom and shortly sit down on his or her bed after the pre-set going to bed time, but without actually going to bed. Therefore, control unit 12 may consider a criterion that generally indicates the beginning of a fasting period to be met only if sensors 4a, 4b provide corresponding and consistent input for some preset minimum time period of, e.g., 15 minutes. An analogue approach may be used to prevent control unit 12 from mistakenly misinterpreting a temporary nocturnal leaving the bed as terminating the fasting period and getting up.

In a further variant, sensors 4a, 4b are physical activity sensors rather than fasting period sensors. Applying the same principals as discussed above in the context of fasting period sensors and using the operational flow as shown in FIG. 3, intervention unit 124a may in such an embodiment be controlled in dependence of physical activity, in particular sportive activity or exercise. In such an embodiment, operative coupling of intervention unit124a and clock unit 123 may or may not be present or may be configurable to be or not to be present.

In further variants, either or both of sensors 4a, 4b may serve as both fasting period sensor and physical activity sensor. For example, sensor 4a may be a GPS receiver that is exclusively used as fasting period sensor as discussed above. Sensor 4b may be a pulse sensor, indicating the beginning of a fasting period if the pulse is below a first threshold of, e.g., 70 beats per minute, and indicating sportive activity if the pulse is above a second threshold of, e.g., 130 beats per minute.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A system for an electronically controlled pump unit, comprising:
    a preset infusion schedule configured to control a pump unit to infuse insulin into a diabetic's body in a substantially continuous manner;
    an intervention unit configured to continuously evaluate a glucose indicative input from a glucose sensor for detecting an actual or expected hypoglycaemia and to execute, in response to an actual or expected hypoglycaemia, a temporary hypoglycaemia intervention, the hypoglycaemia intervention including, for an intervention time interval, overriding the preset infusion schedule by temporarily suspending insulin infusion or temporarily reducing insulin infusion below the preset infusion schedule;
    a control unit configured to operatively coupled to a fasting period sensor and further configured to generate a control signal according to a fasting period measure provided by the fasting period sensor; and
    wherein the control unit is configured to enable execution of the hypoglycaemia intervention upon the fasting period measure indicating that a diabetic associated with the control unit has fallen asleep, has gone to bed, or can be expected to fall asleep or go to bed soon.

2. The system according to claim 1, wherein the intervention unit is configured to execute the hypoglycaemia intervention upon a glucose value of the diabetic falling below a lower intervention threshold.

3. The system according to claim 1, wherein the intervention unit is configured to terminate the hypoglycaemia intervention within a given time interval after starting the hypoglycaemia intervention, or upon a glucose value of the diabetic rising above an upper intervention threshold, or upon a resuming command provided by a user.

4. The system according to claim 1, wherein the control signal includes at least one of a lower intervention threshold, an upper intervention threshold, the reduction of insulin infusion below the preset infusion schedule, and the intervention time interval.

5. The system according to claim 1, wherein the control unit is configured to operatively couple to a physical activity sensor and is configured to generate a second control signal according to the physical activity of the diabetic, the physical activity sensor comprising one or more of an accelerometer, a pedometer, or a pulse meter, an oxymeter, a breath sensor, body temperature sensors, heart rate sensor, ventilation rate sensor, amount of sweat and blood oxygen saturation sensor, EEG sensors and an ECG sensor.

6. The system according to claim 1, wherein the intervention unit is configured to execute, in case of an actual or expected hypoglycaemia of the diabetic, alternative hypoglycaemia handling routines, one of said alternative hypoglycaemia handling routines including executing the hypoglycaemia intervention.

7. The system according to claim 1, wherein the control unit is configured to determine an overshot bolus and a compensation rate based on an amount of insulin that would be infused in accordance with the preset schedule within a compensation time interval following the hypoglycaemia intervention.

8. The system according to claim 1, wherein the intervention unit is configured to adapt its way of operation during execution of the hypoglycaemia intervention.

9. The system according to claim 1, wherein the intervention unit is configured, when executing the hypoglycaemia intervention, to successively reduce insulin infusion and/or, when terminating the hypoglycaemia intervention, to successively resume insulin infusion back to the preset schedule.

10. The system according to claim 1, wherein the intervention unit is configured to determine a level of reduction of insulin infusion below the preset schedule in dependence of the glucose indicative input.

11. The system according to claim 1, wherein the control unit is configured to automatically generate the control signal for the pump unit based on input from the fasting period sensor.

12. A diabetes therapy system, comprising:
    a pump unit configured to be carried by a diabetic; and
    a control unit operatively coupled to the pump unit and configured to control operation of the pump unit, the control unit comprising:
        a preset infusion schedule configured to control the pump unit to infuse insulin into a diabetic's body in a substantially continuous manner;
        an intervention unit configured to continuously evaluate a glucose indicative input from a glucose sensor for detecting an actual or expected hypoglycaemia and to execute, in response to an actual or expected hypoglycaemia, a temporary hypoglycaemia intervention, the hypoglycaemia intervention including, for an intervention time interval, overriding the preset infusion schedule by temporarily suspending insulin infusion or temporarily reducing insulin infusion below the preset infusion schedule;
        wherein the control unit is configured to operative couple to a fasting period sensor and is further configured to generate a control signal according to a fasting period measure provided by the fasting period sensor; and
        wherein the control unit is configured to enable execution of the hypoglycaemia intervention upon the fasting period measure indicating that a diabetic associated with the control unit has fallen asleep, has gone to bed, or can be expected to fall asleep or go to bed soon.

13. The diabetes therapy system according to claim 12, wherein the glucose sensor comprises a continuous glucose monitor.

14. The diabetic therapy system in accordance with claim 12, wherein the control unit is configured to automatically generate the control signal for the pump unit based on input from the fasting period sensor.

* * * * *

UNITED STATES PATENT AND TRADEMARK OFFICE
CERTIFICATE OF CORRECTION

PATENT NO. : 10,080,840 B2
APPLICATION NO. : 15/133485
DATED : September 25, 2018
INVENTOR(S) : Iddo Gescheit and Hans-Juergen Kuhr Page 1 of 1

It is certified that error appears in the above-identified patent and that said Letters Patent is hereby corrected as shown below:

Claim 1, Column 21, Line 47, the phrase "configured to operatively coupled" should read --configured to operatively couple--.

Signed and Sealed this
Sixth Day of November, 2018

Andrei Iancu
*Director of the United States Patent and Trademark Office*